United States Patent
Chen et al.

(10) Patent No.: US 11,344,008 B1
(45) Date of Patent: May 31, 2022

(54) PRODUCTION OF HUMAN DNASEI IN ERYTHROCYTES OF TRANSGENIC NON-HUMAN MAMMAL USING ERYTHROID-SPECIFIC PROMOTER

(71) Applicants: Hai Xing Chen, Toronto (CA); Hong Yang Wang, Shanghai (CN); Zhongtian Qi, Shanghai (CN)

(72) Inventors: Hai Xing Chen, Toronto (CA); Hong Yang Wang, Shanghai (CN); Zhongtian Qi, Shanghai (CN)

(*) Notice: Subject to any disclaimer, the term of this patent is extended or adjusted under 35 U.S.C. 154(b) by 328 days.

(21) Appl. No.: 16/295,155

(22) Filed: Mar. 7, 2019

Related U.S. Application Data

(60) Provisional application No. 62/641,367, filed on Mar. 11, 2018.

(51) Int. Cl.
  *A01K 67/027* (2006.01)
  *C12N 9/22* (2006.01)
  *C12N 15/85* (2006.01)

(52) U.S. Cl.
  CPC ............ *A01K 67/0278* (2013.01); *C12N 9/22* (2013.01); *A01K 2217/052* (2013.01); *A01K 2227/101* (2013.01); *A01K 2227/105* (2013.01); *A01K 2267/01* (2013.01); *C12N 2015/8518* (2013.01)

(58) Field of Classification Search
  CPC ................................. C12N 9/22; A01K 2267/01
  USPC ........................................................ 800/2–21
  See application file for complete search history.

(56) References Cited

U.S. PATENT DOCUMENTS 7,901,671 B2 * 3/2011 Leboulch ............ A61K 48/0058
  424/93.2

OTHER PUBLICATIONS

Gao (Scientific Reports, 2015, vol. 5, 16284, p. 1-13).*
Ohtsuka (Nucleic Acids Res., 2010, vol. 38, No. 22, p. 1-11).*
Mertens (Altex, 2000, vol. 17, No. 1, p. 15-21) abstract only.*
Needham (Nucleic Acids Res., 1992, vol. 20, No. 5, p. 997-1003).*

* cited by examiner

*Primary Examiner* — Michael C Wilson
(74) *Attorney, Agent, or Firm* — CUSPA Technology Law Associates, P.A.; Yi Li

(57) ABSTRACT

A method of producing a non-erythroid protein in erythrocytes of a transgenic animal using an erythroid-specific promoter includes synthesizing an erythroid-specific globin gene promoter and globin gene locus control region and cloning the promoter and the globin gene locus control region and a gene encoding a non-erythroid protein into a vector to obtain a transgene; introducing the transgene in pronuclear embryos collected from a mammalian animal in vitro; transplanting the pronuclear embryos containing the transgene into oviduct of a female recipient of the mammalian animal to obtain a transgenic animal which then expresses the non-erythroid protein in progenitor cells of erythrocytes; and collecting blood from the transgenic animal and isolating the non-erythroid protein from the erythrocytes. Further disclosed are a transgenic animal expressing a non-erythroid protein in progenitor cells of erythrocytes and an isolated erythrocyte of a non-human transgenic animal containing a human non-erythroid protein encoded by a transgene.

9 Claims, 2 Drawing Sheets

PRODUCTION OF HUMAN DNASEI IN ERYTHROCYTES OF TRANSGENIC NON-HUMAN MAMMAL USING ERYTHROID-SPECIFIC PROMOTER

CROSS REFERENCE TO RELATED APPLICATION

This application claims the benefit under 35 USC 119 (e) of the provisional patent application No. 62/641,367, filed Mar. 11, 2018, which is hereby incorporated by reference in its entirety.

FIELD OF THE INVENTION

The present invention relates to a method of producing an exogenous protein in a transgenic animal. In particular it relates to a method of producing a non-erythroid protein selectively in erythrocytes of a transgenic animal using an erythroid-specific promoter.

BACKGROUND OF THE INVENTION

In the past decades, research efforts in gene therapy have been focused on tissue or cell specific approaches. Scientists search for tissue specific genes and methods to deliver these genes into their target organs or tissue, where the proteins are synthesized naturally and are exported and delivered to their functional sites through native pathways. For instance, haemophilia factor XIII and human serum albumin are produced naturally in liver cells and then exported into blood stream for their functions. Insulin is produced in pancreas beta-cells and also exported into blood stream for its function.

Although specific delivery of therapeutic genes into their native manufacturing sites is the ideal scheme for gene therapy, it is difficult to practice either in vivo or in vitro. In vitro, it is almost impossible to harvest enough target cells to introduce therapeutic genes into them, and in turn, these target cells are not able to synthesize sufficient amount of proteins for the purpose of therapy. In vivo, a therapeutic gene has an equivalent probability entering any type of cells, whether they are in the form of retroviral vector, liposome harbored retroviral vector or naked DNA. Consequently, few of the DNA (therapeutic gene) will be delivered into its target cells. Therefore, the success of existing gene therapy approaches depends on whether a tissue specific gene can be delivered specifically to the target organ or tissue.

On the other hand, non-tissue specific approaches also encounter serious obstacles. Although many cell types in the body are easy to obtain, such as muscle or skin cells, there are disadvantages associated with using non-tissue specific cells as host cells for gene therapy. In some cases, host cells do not naturally possess protein export mechanisms. In other cases, even if the host cells possess natural export mechanisms for their native proteins, they may not function equivalently in exporting a non-native or guest protein. Low efficiency in exporting a guest protein or complete blockage of a native export pathway has been reported.

One of the earliest gene therapy for curing human diseases was to use genetic engineered hemoglobin for treating beta thalassemia, a disorder of hemoglobin. Erythrocytes of patients having beta thalassemia are deficient in beta globin. The lack of beta globin gives rise a deficit in hemoglobin production, which in turn causes severe anemia. Researchers used beta globin promoter and beta globin gene (native to the erythrocytes) to produce the desired beta globin. In these approaches, the hemoglobin promoter is not utilized in genetic engineering of heterologous proteins (non-native to the erythrocytes) in erythrocytes.

In recent years, some nonviral methods for therapeutic gene transfer have also been developed. For instance, injection of naked DNA (without lipid wrapping) into patients has been explored. The naked DNA, injected into the muscle of an animal, expressed protein with a relatively high local concentration. However, the local high concentration of protein produced inside the muscle would not have been sufficient to be effective against diseases like diabetes or hemophilias when the proteins are diluted into about three liters of plasma contained in the blood stream of a person.

Therefore, there is a need to overcome difficulties in the field of gene therapy and a need of new methods for producing proteins that can be delivered through blood stream of a patient.

SUMMARY OF THE INVENTION

In some embodiments, the present invention is directed to a method of producing a non-erythroid protein in erythrocytes of a transgenic animal using an erythroid-specific promoter. In one embodiment, the method comprises synthesizing an erythroid-specific globin gene promoter and globin gene locus control region, respectively, and cloning the erythroid-specific globin gene promoter and globin gene locus control region and a gene encoding a non-erythroid protein into a vector to obtain a transgene comprising the erythroid-specific globin gene promoter and globin gene locus control region and the gene encoding the non-erythroid protein, wherein the erythroid-specific globin gene promoter and globin gene locus control region and the gene encoding the non-erythroid protein are operably linked; introducing the transgene in pronuclear embryos collected from a donor of a mammalian animal in vitro; transplanting the pronuclear embryos containing the transgene into oviduct of a female recipient of the mammalian animal to obtain a transgenic animal having the transgene stably integrated into a genome of the transgenic animal, wherein the transgenic animal expresses the non-erythroid protein in progenitor cells of erythrocytes, resulting in the erythrocytes containing the non-erythroid protein; and collecting a volume of blood from the transgenic animal, separating the erythrocytes from other blood cells, and isolating the non-erythroid protein from the erythrocytes.

In other embodiments, the present invention is directed to a transgenic animal expressing a non-erythroid protein in progenitor cells of erythrocytes wherein the non-erythroid protein is encoded by a transgene stably integrated into a genome of the transgenic animal and wherein the transgene comprises an erythroid-specific globin gene promoter and globin gene locus control region and a gene encoding the non-erythroid protein, in which the erythroid-specific globin gene promoter and the globin gene locus control region and the gene encoding the non-erythroid protein are operably linked.

In further embodiments, the present invention is directed to an isolated erythrocyte of a non-human transgenic animal comprising a human non-erythroid protein encoded by a transgene stably integrated into a genome of the transgenic animal and wherein the transgene comprises an erythroid-specific globin gene promoter and globin gene locus control region and a gene encoding the human non-erythroid protein, in which the erythroid-specific globin gene promoter and globin gene locus control region and the gene encoding the human non-erythroid protein are operably linked.

The advantages of the present invention will become apparent from the following description taken in conjunction with the accompanying drawings showing exemplary embodiments of the invention.

DETAILED DESCRIPTION OF THE INVENTION

Figure 1:
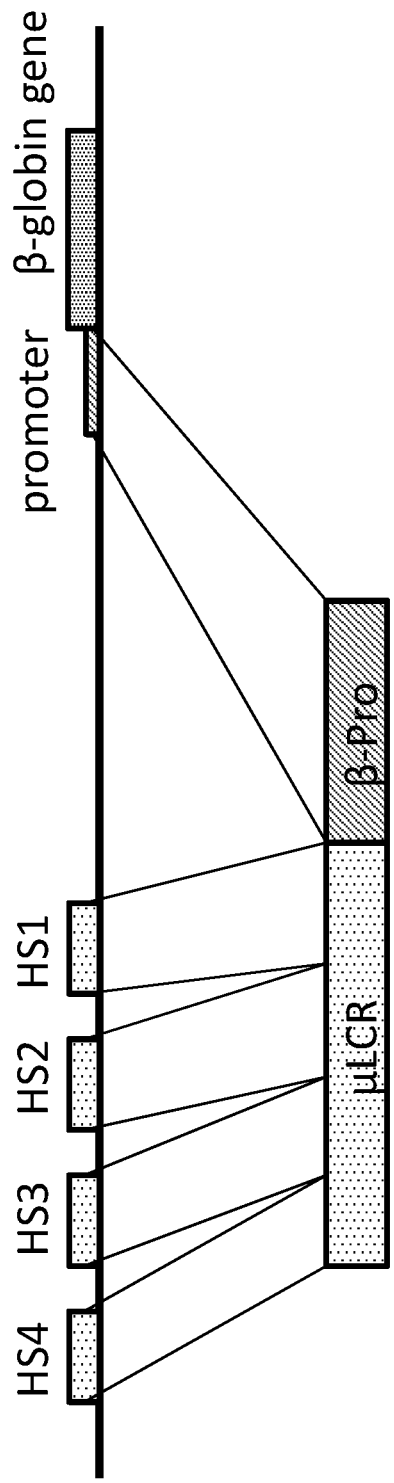
FIG. 1 schematically illustrates a promoter and an enhancer for making a transgenic animal with the present method.

Embodiments of the present invention generally relate to a method of producing a non-erythroid protein in erythrocytes of a transgenic animal using an erythroid-specific promoter as well as such a transgenic animal. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In some embodiments, the present invention provides a method for producing a non-erythroid protein in erythrocytes of a transgenic animal using an erythroid-specific promoter. In one embodiment, the method comprises
a. synthesizing an erythroid-specific globin gene promoter and globin gene locus control region, respectively, and cloning the erythroid-specific globin gene promoter and globin gene locus control region and a gene encoding a non-erythroid protein into a vector to obtain a transgene comprising the erythroid-specific globin gene promoter and globin gene locus control region and the gene encoding the non-erythroid protein, wherein the erythroid-specific globin gene promoter and globin gene locus control region and the gene encoding the non-erythroid protein are operably linked;
b. introducing the transgene in pronuclear embryos collected from a donor of a mammalian animal in vitro;
c. transplanting the pronuclear embryos containing the transgene into oviduct of a female recipient of the mammalian animal to obtain a transgenic animal having the transgene stably integrated into a genome of the transgenic animal, wherein the transgenic animal expresses the non-erythroid protein in progenitor cells of erythrocytes, resulting the erythrocytes containing the non-erythroid protein; and
d. collecting a volume of blood from the transgenic animal, separating the erythrocytes from other blood cells, and isolating the non-erythroid protein from the erythrocytes.

In some exemplary embodiments, the erythroid-specific globin gene promoter is human β-globin gene promoter, and the globin gene locus control region is a locus control region of human β-globin gene cluster, which is an enhancer.

The term "promoter" as used herein connotes in its broadest sense any promoter which enables initiation of a gene to express a protein in the progenitor cells of the erythrocytes. The promoter could be a natural promoter of a gene, or a mutated promoter of a gene. A natural promoter is the promoter present in the gene of a protein that is native to the cell. Optionally, the promoter may be present in tandem with another promoter, and may include one or more enhancer elements. In one embodiment, the promoter is an erythroid-specific human β-globin gene promoter. The term "enhancer" used herein includes any enhancer capable of increasing the utilization of promoters, and functioning in either orientation and in any location (upstream or downstream) relative to the promoter. For the purpose of the present invention, the enhancer is erythroid-specific. The term "gene" as used herein is a DNA sequence, preferably a structural gene encoding a protein.

The term "non-erythroid protein" used herein refers to any protein that is not naturally present in erythrocytes, and in other words, it is an exogenous protein. The non-erythroid protein for the purpose of the present invention includes, but not limited to, antibody, enzyme, cofactor, interferon, hormone, and peptide. Furthermore, the non-erythroid protein may include natural protein, fusion protein and mutated protein. The protein can be entirely heterologous to the host cell. The protein may also be a commercially useful polypeptide or peptide, such as a pharmaceutical. Herein, the non-erythroid protein is also referred to as a subject protein that is produced with the present method.

Herein, "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called "transgene" and may contain one or many genes, cDNA, etc. The transgene is exogenous to the genome of the transgenic animal. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the foreign nucleic acid into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell.

The term "vector" as used herein connotes in its broadest sense any recombinant DNA material capable of transferring DNA from one cell to another. The vector can be a single piece of DNA in linear or circular form, and can, in addition to the essential functional elements of the invention, include such other sequences as are necessary for particular applications. For example, the vector may contain additional features such as a selectable marker gene or genes, and/or features which assist translation or other aspects of the production of a cloned product.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (namely, the coding sequence is under the transcriptional control of the promoter).

In some embodiments, the transgenic animal is a non-human mammalian animal. Herein, the term of "non-human" animal refers to any animal of a species that is not human. For example, in exemplary embodiments transgenic mice and goat are used to produce a subject protein using the method of the present invention. To harvest abundant subject protein from peripheral blood of a transgenic animal, large animals such as goat, sheep and cow may be used.

The method of the present invention is further described with exemplary embodiments. In some embodiments, expression of a non-erythroid protein in erythrocytes of a transgenic animal is performed using a human β-globin gene promoter (0.9 kb upstream of β-globin gene), hereinafter referred to as β-Pro, in combination with locus control region (LCR) of human β-globin gene cluster as an enhancer. The human β-globin gene cluster, which extends over 70 kb of chromosome 11, contains five globin genes (ε, $^G$γ, $^A$γ, δ, and β), arranged in the same orientation and in the order of their expression during development. Several kilobases upstream of the ε-globin gene are at least five DNase I-hypersensitive sites (HS1 to HS5) which constitute the locus control region (LCR). It was reported previously the human β-globin gene promoter (β-Pro) plus a core region of HS1-HS4 (about 3.1 kb, µLCR) control protein expression specifically in erythrocytes (The Journal of Biological Chemistry 1998, p 17361). In one embodiment, known sequences of the core region of HS1-HS4 of the locus control region of human β-globin gene cluster and human β-globin gene promoter (Gene Bank No.: Humhbb) are used to synthesize erythroid-specific µLCR/β-Pro, as illustrated in FIG. 1, which is subsequently cloned into a pBluescript II KS vector.

Figure 2:
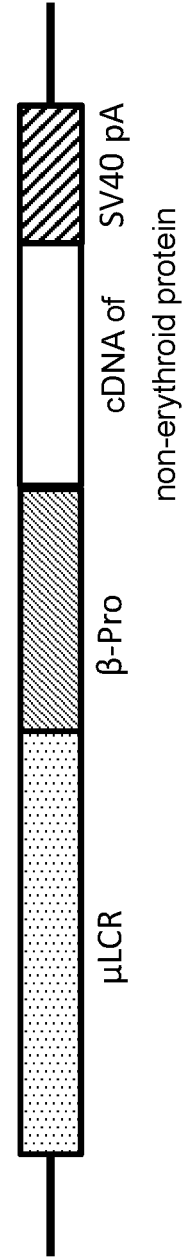
FIG. 2 schematically illustrates construction of a transgenic vector using an erythroid-specific promoter and enhancer for producing a non-erythroid protein by a transgenic animal.

To construct a vector for a transgenic animal, the cDNA of a subject protein is cloned downstream of the µLCR/β-Pro and upstream of SV40 PA (SV40 PolyA sequence) as illustrated in FIG. 2. The transgene including µLCR/β-Pro, cDNA of a subject protein and SV40 PA is removed by restriction enzyme digestion and purified by Gel-Based DNA Purification method.

In some embodiments, a transgenic mouse can be made using the purified transgene to produce the subject protein. The purified transgene can be microinjected into the pronuclear embryos of C57BL/6 mouse. Following an incubation at 37° C. with 5% $CO_2$, the embryos are transplanted into oviduct of recipient pseudo-pregnant female mice. Mouse tail genomic DNA from new born mice is used for genotyping by PCR. The expression level of the subject protein can be measured by western blotting. Properties and functions, such as therapeutic effect to certain clinical conditions of the subject protein expressed by the transgenic mouse, can be evaluated using known methods.

In some embodiments, a transgenic goat is made using the purified transgene described above to produce the subject protein. Upon confirmation of desired function and properties of the subject protein produced by the transgenic mice, the subject protein can be produced in the erythrocytes of the transgenic goat to achieve abundant quality of the protein. Goat is an animal widely used for the production of recombinant pharmaceutical proteins in milk. The same vector described above in making transgenic mice may be used except that a His-Tag is fused with the cDNA of the subject protein to facilitate protein purification. Purified transgene described above may be injected in pronuclear goat embryos. To evaluate the post-injection survival, the embryos can be cultured for 1-2 hours at 37° C. with 5% $CO_2$. The surviving zygotes may then be transferred to recipient goats. The transgenic founders may be detected in skin biopsies from the ears of two-week-old transgenic goats using PCR amplification, and expression of the subject protein in erythrocytes of the transgenic goats can be tested by western blotting.

The erythrocytes produced by the transgenic goats can be collected from peripheral blood of the transgenic goats and the subject protein contained in erythrocytes can be isolated and purified. In one example, a volume of peripheral blood is drawn from the transgenic goats. The blood is centrifuged, then the plasma and leukocytes are removed. The erythrocytes are then washed with a saline, and then lysed with an aqueous lysing reagent. The subject protein in the lysate is purified using high performance liquid chromatography (HPLC). In the purified protein, the His-Tag can be removed by TEV protease digestion if the His-Tag inhibits functions of the subject protein.

The present method is further illustrated in the example, in which recombinant human deoxyribonuclease (rhDNase I), a non-erythroid protein, is produced by transgenic mice and transgenic goats. It is known that respiratory distress and progressive lung destruction can be attributed to the accumulation and persistence of viscous purulent secretions in the airways of the lung. DNA may contribute to the increased viscosity of lung secretions because DNA is extremely viscous polyanion and presents in very large amounts (3-14 mg/ml) in purulent secretions. Recombinant human deoxyribonuclease (rhDNase I) depolymerizes extracellular DNA and reduces the viscoelasticity of purulent airway secretions. Treatment with rhDNase I effectively improves pulmonary function of patients suffering from cystic fibrosis.

Figure 3:
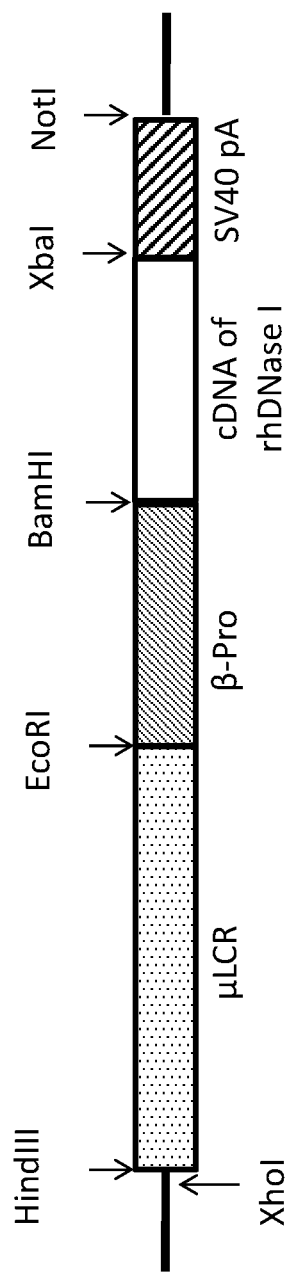
FIG. 3 illustrates an exemplary transgenic vector as described in the example.

As illustrated in the example, production of rhDNase I in erythrocytes of a transgenic animal is performed using a human β-globin gene promoter (β-Pro) and a core region of HS1-HS4 of the locus control region of human β-globin gene cluster (µLCR). Human β-globin gene promoter (β-Pro) and the core region of HS1-HS4 (µLCR) are synthesized, respectively, using known sequences of human β-globin gene promoter and a core region of HS1-HS4 of the locus control region of human β-globin gene cluster (Gene Bank No.: Humhbb). Then, the synthesized µLCR is cloned into HindIII and EcoRI sites of a pBluescript II KS vector, and the synthesized β-Pro is cloned into EcoRI and BamHI sites of the pBluescript II KS vector, respectively, as illustrated in FIG. 3. The cDNA of rhDNase I is commercially available and can be purchased from GE Healthcare (clone ID 4594247). To create a vector for transgenic mouse, the cDNA of rhDNase I is cloned into BamHI and XbaI sites downstream of the β-Pro and upstream of SV40 PA (SV40 PolyA sequence) in the pBluescript II KS vector, as shown in FIG. 3.

In the example, pronuclear embryos from a pseudo-pregnant female mouse is microinjected with the purified transgene in vitro, and the pronuclear embryos containing the transgene are transplanted into oviduct of a female recipient mouse to obtain transgenic mice. Similarly, transgenic goats are made using the purified transgene to produce abundant amount of rhDNase I. The erythrocytes containing rhDNase I can be collected from peripheral blood of the transgenic animals and rhDNase I can be isolated from the erythrocytes and purified for use in treatment of cystic fibrosis.

In further embodiment, the present invention is directed to a transgenic animal genetically produced with the present method. As discussed above, the transgenic animal expresses a non-erythroid protein in progenitor cells of erythrocytes wherein the non-erythroid protein is encoded by a transgene stably integrated into a genome of the transgenic animal. The transgene comprises an erythroid-specific globin gene promoter and globin gene locus control region and a gene encoding the non-erythroid protein, in which the erythroid-specific globin gene promoter and globin gene locus control region and the gene encoding the non-erythroid protein are operably linked.

Moreover, in another embodiment, the present invention is directed to an isolated erythrocyte of a non-human transgenic animal genetically produced with the present method. The isolated erythrocyte comprises a human non-erythroid protein encoded by a transgene stably integrated into a genome of the transgenic animal. The transgene comprises an erythroid-specific globin gene promoter and globin gene locus control region and a gene encoding the human non-erythroid protein, in which the erythroid-specific globin gene promoter and globin gene locus control region and the gene encoding the human non-erythroid protein are operably linked.

The present method has several advantages in production of a protein in vivo. The present method can produce abundant protein in vivo which fulfils a need of certain human proteins for therapeutic purposes, which may be difficult to obtain with existing technologies. Since erythrocyte production is a continuous process in the transgenic animal, the protein is synthesized in a continual manner.

With the present method, a protein is only contained in erythrocytes because the erythroid-specific globin gene promoter is active only in progenitor cells of erythrocytes. Erythrocytes are a temporary storage site for the protein before harvesting. This is a major distinction between erythrocytes and other nucleated blood cells such as leukocytes. The latter is capable of protein expression in the peripheral blood. The erythrocytes provide a natural protection to the protein produced against degradation. Mature erythrocytes contain mainly hemoglobin and cytoplasm and there is no nucleus in mature erythrocytes. Compared to nucleated cells, the protein produced will be more stable in the erythrocytes, since the protein in erythrocytes is not exposed to and will not be degraded by nuclear enzymes. In addition, the erythrocytes also protect the protein from extra-cellular environment before the protein being harvested.

The protein produced by the transgenic animal can be delivered into peripheral blood of a human patient who is in need of a treatment with a supply of the protein. Such a delivery of a needed protein avoids limitations of natural cell function. More specifically, the method avoids the difficulty in protein export or delivery by host cells if the host cells used are not the cells of the specific organ or tissue that naturally produce the protein. For example, certain proteins generated in skin tissue by genetic method have to be adequately released from the host skin tissue cells before it can be utilized in the blood stream for therapeutic purpose. Since the host cells are not the original organ or tissue cells in the natural protein production process, they may not have secretion function to export a specific guest protein. In the latter case, the guest protein will accumulate in the host cells and cause cell death eventually.

Therefore, the protein produced by the present method can have broad scope applications in treating diseases, either inherited genetically or acquired diseases. In general, any protein that either has a function in blood stream, such as hemophilia factor XIII, or can be delivered to functional site through blood stream, such as hormones, can be supplied by direct delivery into peripheral blood of a patient.

One suitable application is to treat inherited diseases, such as cystic fibrosis, duchenne muscular dystrophy, hemophilia A, Huntington's disease, familial hypercholesterolemia, and fragile-X syndrome. A further application is to provide a protein that functions as an enzyme for the treatment of other diseases, such as Gauchers disease. Another application is to provide a protein that functions as a hormone. Suitable examples of proteins include thyroid hormone and growth hormone.

Moreover, a further application is to treat decreased protein level caused by certain conditions. Suitable examples include low level of human serum albumin produced by liver, low level of hemoglobin stimulation factor, cortisol deficiency, and aldosterone deficiency caused by certain kidney conditions. Certain pituitary gland conditions caused by growth hormone deficiency, gonadotropin deficiency, thyroid stimulating hormone deficiency, and adrenal cortex deficiency may also be treated by supplying a desired protein. Another application is to provide a mammalian or a non-mammalian protein that has a therapeutic function. Suitable examples of such proteins include animal protein (e.g. snake), micro-organism protein (e.g. interferon), and plant protein with a therapeutic function.

Additionally, a further application is to provide proteins related to cancers. Suitable examples of proteins are anti-oncogene (tumor inhibitor) protein, tumor necrosis gene protein, and interferon. It is known that in different types of cancer patients, certain proteins are missing or low in concentration in comparison to normal subjects. Lack of certain proteins may be responsible for malignant cell growth, or may cause severe damage of the immune or metabolic system of the cancer patient. A supply of certain protein can have therapeutic effects in the former case, or reduce symptoms or complications for the latter. Moreover, a supply of certain proteins may also have a preventative effective to certain types of cancers. This is particularly suitable for those cancer high risk populations that inherited genetic defects in their natural protein production capability. Well known examples are breast cancer, ovarian cancer, and prostate cancer. Existing tissue specific methods may not work effectively in such situation, because the target tissue or cells may not be compatible with gene-transferred cells due to the inherited genetic defects.

In addition, a further application is to provide proteins to treat immune system diseases. Suitable examples of diseases are antibody deficiency syndromes, such as Bruton's agam-maglobinemia (reduced IgG, IgM, and IgA), common variable immunodeficiency (reduced IgG, IgM, and IgA), and selective IgA deficiency (reduced IgA). Another example is the phagocyte disorders, such as C1r, C1q, C2 defection, C4 defection, C3 defection, and C5-C9 defection.

The present method is further described by following example, which is intended to be illustrative and not limiting.

Example

Production of recombinant human deoxyribonuclease (rhDNase I), a non-erythroid protein, in erythrocytes of a transgenic animal is performed using a human β-globin gene promoter and a locus control region (LCR) of human β-globin gene cluster with the following process:

Preparing Erythroid-Specific Promoter and Enhancer

A human β-globin gene promoter (0.9 kb upstream of human β-globin gene, β-Pro), and a core region of HS1-HS4 of the locus control region of human β-globin gene cluster (about 3.1 kb, μLCR) are synthesized, respectively, using known sequences of human β-globin gene promoter and core region of HS1-HS4 (Gene Bank No.: Humhbb). Then, the synthesized μLCR is cloned into HindIII and EcoRI sites of a pBluescript II KS vector, and the synthesized β-Pro is cloned into EcoRI and BamHI sites of the pBluescript II KS vector, respectively, as shown in FIG. 3.

Constructing a Vector for Transgenic Animal cDNA of rhDNase I can be purchased from GE Healthcare (clone ID 4594247). To create a vector for transgenic mouse, the cDNA of rhDNase I is cloned into BamHI and XbaI sites downstream of the β-Pro and upstream of SV40 PA (SV40 PolyA sequence) in the pBluescript II KS vector, as shown in FIG. 3.

The transgene including μLCR/β-Pro, cDNA of rhDNase I and SV40 PA is removed by restriction enzyme digestion with restriction enzymes XhoI and NotI, and purified by Gel-Based DNA Purification method.

Making a Transgenic Mouse

A transgenic mouse is made using the purified transgene described above to produce rhDNase I. The purified transgene is microinjected into the pronuclear embryos of C57BL/6 mouse. Following a 20 minute incubation at 37° C. with 5% $CO_2$, the embryos is transplanted into oviduct of pseudo-pregnant female recipient mice. Mouse tail genomic DNA from new born mice is used for genotyping by PCR to confirm the transgene. The expression level of rhDNase I can be measured by western blotting. The property and functions such as therapeutic effect to certain clinical conditions of the expressed rhDNase I can be evaluated using known methods.

Making a Transgenic Goat

Upon confirmation of desired function and properties of rhDNase I produced by the transgenic mice described above, rhDNase I is then produced in goat for obtaining abundant quality of the protein. The same vector described above in making transgenic mouse is used except that a His-Tag is fused with the cDNA of the expressed protein to facilitate protein purification. Purified transgene described above is injected into pronuclear goat embryos. To evaluate the post-injection survival, the embryos are cultured for 1-2 hours at 37° C. with 5% $CO_2$. The surviving zygotes will then be transferred to recipient goats. The transgenic founders may be detected in skin biopsies from the ears of two-week-old transgenic goats using PCR amplification, and expression of rhDNase I in erythrocytes of the transgenic goats can be tested by western blotting.

Purification of Expressed Protein from Erythrocytes

A volume of peripheral blood is drawn from the transgenic goat. The blood is centrifuged at 800 g for 10 minutes, then the plasma and leukocytes are removed. The separated erythrocytes are washed with 2 volume of 0.9% NaCl saline solution and then lysed with 2 volume of an aqueous lysing reagent which contains 1 mM dithiothreitol (DTT), 1 mM potassium phosphate ($MgCl_2$), and 0.5% octyl phenol ethoxylate ether (Triton™ X-100), pH7.6 to release rhDNase I contained in the erythrocytes. rhDNase I in the lysate is purified using high performance liquid chromatography (HPLC) with a HisTrap™ High Performance column (GE Healthcare, Baie d'Urfe, Quebec, Canada). The His-Tag can be removed by TEV protease digestion if it inhibits functions of the protein.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

All patents and publications referred to in this application are hereby incorporated by reference in their entirety.

What is claimed is:

1. A method of producing human deoxyribonuclease I (hDNase I) in erythrocytes of a transgenic non-human mammal, the method comprising:
   (a) synthesizing a transgene comprising a nucleic acid sequence encoding hDNase I operably linked to an erythroid-specific promoter-enhancer comprising a human β-globin promoter and a human β-globin locus control region (LCR);
   (b) introducing the transgene into pronuclear non-human mammalian embryos in vitro;
   (c) transplanting the pronuclear non-human mammalian embryos obtained in step b) into a recipient female such that a transgenic non-human mammal whose genome comprises a nucleic acid sequence encoding hDNase I operably linked to the erythroid-specific promoter-enhancer is obtained, wherein erythrocytes of the transgenic non-human mammal contain hDNase I; and
   (d) isolating hDNase I from the erythrocytes in the blood of the transgenic non-human mammal.

2. The method of claim 1, wherein the human β-globin promoter is a 0.9 kb nucleic acid sequence that is upstream of a human β-globin coding region within a human β-globin gene.

3. The method of claim 1, wherein the human β-globin LCR contains a core region of human β-globin DNase I-hypersensitive sites HS1, HS2, HS3 and HS4.

4. A transgenic non-human mammal whose genome comprises a nucleic acid sequence encoding human deoxyribonuclease I (hDNase I) operably linked to an erythroid-specific promoter-enhancer comprising a human β-globin promoter and a human β-globin locus control region (LCR), wherein erythrocytes of the m mal contain the hDNase I.

5. The transgenic non-human mammal of claim 4, wherein the human β-globin promoter is a 0.9 kb nucleic acid sequence that is upstream of a human β-globin coding region within a human β-globin gene.

6. The transgenic non-human mammal of claim 4, wherein the human β-globin LCR contains a core region of human β-globin DNase I-hypersensitive sites HS1, HS2, HS3 and HS4.

7. An isolated erythrocyte of a transgenic non-human mammal whose genome comprises a nucleic acid sequence encoding human deoxyribonuclease I (hDNase I) operably linked to an erythroid-specific promoter-enhancer comprising a human β-globin promoter and a human β-globin locus control region (LCR), wherein the erythrocyte of the mammal contains hDNase I.

8. The isolated erythrocyte of claim 7, wherein the human β-globin promoter is a 0.9 kb nucleic acid sequence that is upstream of a human β-globin coding region within a human β-globin gene.

9. The isolated erythrocyte of claim 7, wherein the human β-globin LCR contains a core region of human β-globin DNase I-hypersensitive sites HS1, HS2, HS3 and HS4.

* * * * *